US005453092A

United States Patent [19]

Merriman

[11] Patent Number: 5,453,092
[45] Date of Patent: Sep. 26, 1995

[54] LOCKING SYSTEM FOR HYPODERMIC SYRINGES

[76] Inventor: Grant B. Merriman, 49 Lost Creek La., #308, Murray, Utah 84107

[21] Appl. No.: 270,763

[22] Filed: Jul. 5, 1994

[51] Int. Cl.$^6$ ........................................... A61M 5/00
[52] U.S. Cl. ................................. 604/110; 604/218
[58] Field of Search .............................. 604/110, 187, 604/218, 220, 221, 228, 225

[56] References Cited

U.S. PATENT DOCUMENTS

| | | | |
|---|---|---|---|
| 4,713,056 | 12/1987 | Butterfield | 604/110 |
| 4,878,899 | 11/1989 | Plouff | 604/110 |
| 4,932,941 | 6/1990 | Min et al. | 604/110 |
| 4,973,316 | 11/1990 | Dysarz | 604/110 X |
| 5,019,044 | 5/1991 | Tsao | 604/110 |
| 5,021,047 | 6/1991 | Movern | 604/110 |
| 5,045,063 | 9/1991 | Spielberg | 604/218 X |
| 5,308,331 | 5/1994 | Avila et al. | 604/110 |

*Primary Examiner*—John D. Yasko
*Attorney, Agent, or Firm*—Henry S. Miller; Rhodes & Ascolillo

[57] ABSTRACT

A locking system for hypodermic syringes including a barrel and pistons where the barrel contains a plurality of detentes surrounding the piston in the "full in" position. A floating ring slides in a channel on the piston, restraining the detentes from engaging the piston head in the packaged position. In use the floating ring slides away from the piston head allowing the detentes to secure the piston in the "full in" position. Subsequent attempts to withdraw the piston will disengage the piston shaft form the piston.

2 Claims, 6 Drawing Sheets

LOCKING SYSTEM FOR HYPODERMIC SYRINGES

BACKGROUND OF THE INVENTION

1. Field of the Invention

This invention relates to medical equipment and in particular to non-reusable hypodermic syringes.

2. Description of the Prior Art

If not the most widely used medical tool, the hypodermic syringe is near the top of any list on the subject. Since it has both legal and illegal uses it is important that the syringe be used correctly. It is well known that the syringe in the hands of a drug user is an instrument of the devil, not only for the injection of illegal drugs but also the spread of disease caused by reuse of the same needle. Although not generally thought of as sinister, the reuse of the syringe in cases of mass immunizations, particularly in third world countries, has at least the same potential for spreading disease but among an innocent, defenseless population.

Recently, with the introduction of AIDS into the drug formula, especially for the intravenous user, there has been a serious attempt to control the spread of the disease through the control of needles or syringes used in the process. For example, U.S. Pat. No. 4,713,056 issued Dec. 15, 1987 to Butterfield, shows a non-reusable hypodermic syringe that utilizes a lock ring (10) that is located in groove (14) of the barrel (12). As piston (16) passes the lock ring, fingers (26) deflect allowing it to move in one direction and expel the contents of the barrel, however the fingers will not allow the piston to retract and be reused. U.S. Pat. No. 4,878,899 issued Nov. 7, 1989 to Plouff discloses a disposable syringe that uses a plurality inwardly extending arms that slide over the plunger which then restrain the plunger from any further movement. In the U.S. Pat. No. 4,932,941 issued Jun. 12, 1990 to Min et al. a disposable syringe is shown that utilizes a set of inwardly directed tapered notches (5) that restrain the piston from retraction once it has travelled its full stroke and discharged its contents. The Safety Hypodermic Syringe of Tsao disclosed in U.S. Pat. No. 5,019,044 issued May 28, 1991 shows a plunger shaft having a displaceable plug (56) in alignment with a needle holder plate (34), when the shaft has travelled full stroke the plug is displaced by the plate which engages the walls of the aperture and is dislocated along with the needle as the shaft is retracted, FIGS. 3 and 4. U.S. Pat. No. 5,021,047 issued Jun. 4, 1991 to Movern is drawn to a restricted use syringe utilizing teeth on means attendant to the plunger shaft in cooperation with annular corrugations on the interior surface of the syringe wall to prevent retraction of the piston shaft.

The prior art clearly demonstrates the need for a hypodermic syringe that is safe, reliable and discourages attempts for reuse.

SUMMARY OF THE INVENTION

The invention is directed to a hypodermic syringe that provides all the advantages of the prior art and none of the disadvantages. A typical barrel shaped structure is closed at one end and equipped with a brace that supports a hypodermic needle in communication with the interior, fluid containing area. Positioned about the barrel, on the outside in two nearly semi-circular segments are a plurality of detent locks, encased in barrel material and forming a part of the barrel. The detent locks are spring biased to extend into the interior of the barrel near the brace. A piston shaft extends from a piston within the barrel on one end to beyond the limit of the barrel on the other end. The piston is in a fluid tight, axial translating position in the barrel and contains a circumferential channel adapted to accommodate a floating ring. The floating ring engages the interior wall of the barrel and is in a loose fit with the piston body. In the unused packaged condition the floating ring is in juxtaposition with the head or leading component of the piston. The floating ring restrains the detent locks, against the spring bias, from entering the interior of the barrel.

In use, as the piston is retracted from the packaged or "full in" position, the detent locks ride against the floating ring and then against the head of the piston. As the head of the piston passes, the detent locks yield to the force of the spring bias and move beyond the interior wall of the barrel into a blocking position. When the volume between the leading edge of the piston and the needle is filled with fluid the piston direction is reversed and the piston, via the piston shaft, is moved toward the needle communication port in order that the fluid be dispensed. The floating ring momentarily remains in place relative to the interior wall and is finally moved by the opposite edge of the channel. This leaves a substantial space between the head of the piston and the floating ring. As the piston head engages the protruding detent locks, having the appropriate slope to their top edge, they slide over the beveled surface of the piston back into their original position and, since the floating ring is now at the other side of the channel, the detent locks re-extend into the interior of the barrel above the piston head and prevent the piston from any further axial movement.

It is therefore an object of the invention to provide a new and improved locking system for hypodermic syringes.

It is another object of the invention to provide a new and improved locking system for hypodermic syringes that is more reliable than similar known prior art devices.

It is a further object of the invention to provide a new and improved locking system for hypodermic syringes that is low in cost.

It is still another object of the invention to provide a new and improved locking system for hypodermic syringes that may be easily and efficiently manufactured and marketed.

It is still a further object of the invention to provide a new and improved locking system for hypodermic syringes that allows for a single use only.

These and other advantages, features and objects of the invention will become more apparent from the following description taken in connection with the illustrative embodiment in the accompanying drawings.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE PREFERRED EMBODIMENT

Figure 1:
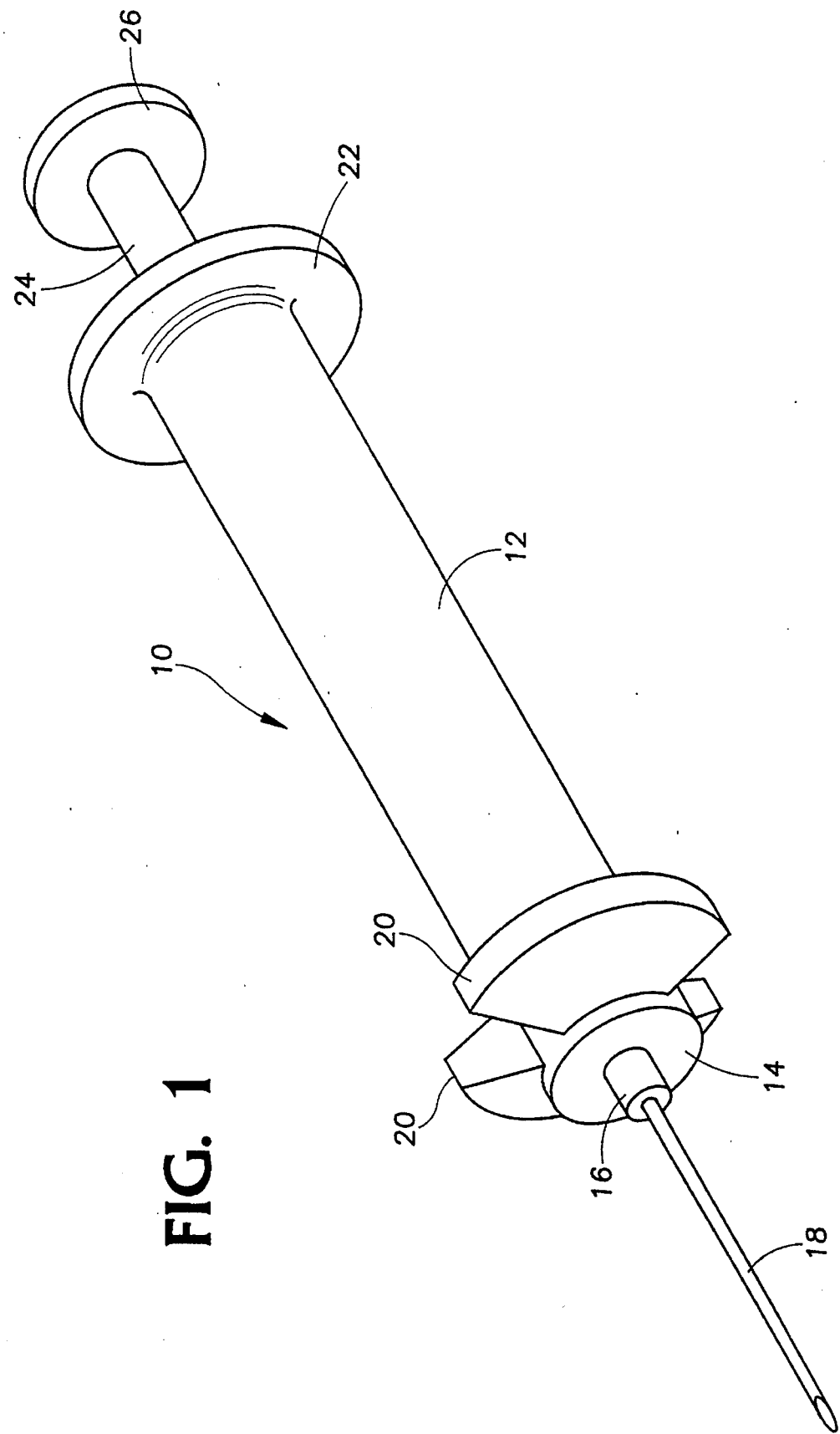
FIG. 1 is a perspective view of the hypodermic syringe of the invention.

Referring now to FIG. 1, the syringe of the invention is shown generally at 10. A cylindrically shaped barrel 12 is closed at one end 14 with a brace 16 supporting a needle 18 which communicates with the interior of the barrel. A pair of generally semi-circular enclosures 20 are formed proximal the closed end of the barrel and contain a plurality of locking detents as will be described hereinafter. The distal end of the barrel is generally open and includes a lip 22 for grasping the barrel during a fluid injection process. A piston shaft 24 is shown extending beyond the limits of the barrel and includes a thumb button 26 for applying pressure to the shaft during the injection process.

Figure 2:
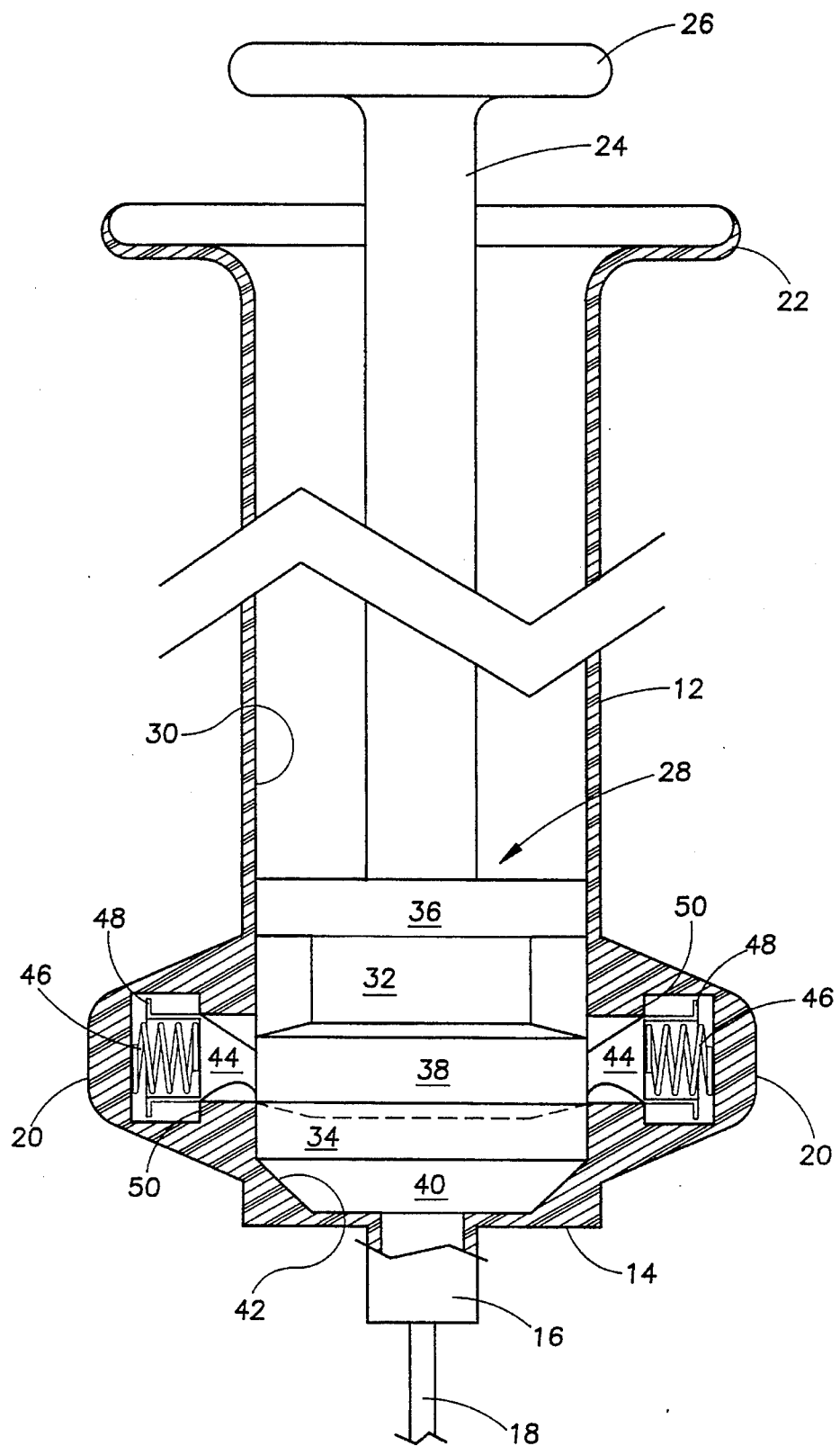
FIG. 2 is a cutaway view showing the internal components of the invention in the packaged or "full in" position.

Concerning FIG. 2, the interior components are shown in their packaged or "full in" position. Shaft 24 is connected to a piston shown generally at 28. The piston is in a fluid tight fit with the interior wall of the barrel 30. The piston is cylindrically shaped and includes a circumferentially located channel 32 approximately mid-way between the head or leading edge of the piston 34 and the trailing edge 36. A floating ring 38 is adapted to slide axially within the channel 32. The face of the piston 40 is beveled and mates with the interior surface 42 of the closing member 14.

Figure 3:
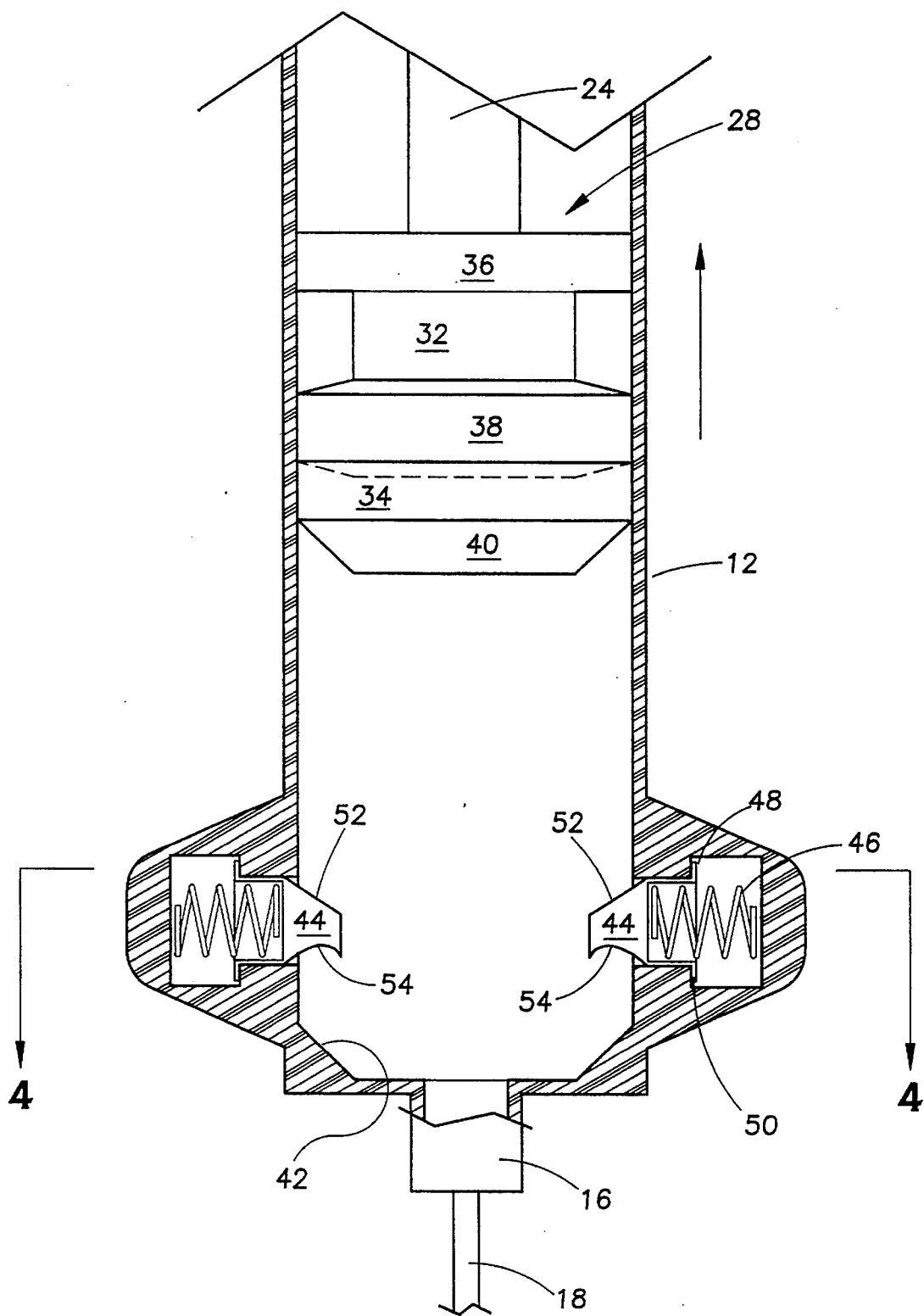
FIG. 3 is a cutaway view showing the internal components of the invention in the retracted condition.

A plurality of locking detents 44 located in the enclosures 20 are biased inwardly by springs 46 and are restrained by floating ring 38 in the "full in" condition shown in the figure. Detent limiters 48 move against the shoulder 50 when other restraint means are removed to prevent the spring bias from dislocating the detent means from their location, as shown in FIG. 3. Referring to FIG. 3, the locking detents 44 are shaped with a slope 52 which is compatible with the beveled face 40 of the piston 28. This shape allows the piston, when moving into the closing condition to displace the detents against the bias of the spring and pass into the closed condition. The arcuate shape 54 causes the detent to engage the leading edge of the piston 34 locking it in place and preventing further movement as will be described hereinafter.

Figure 4:
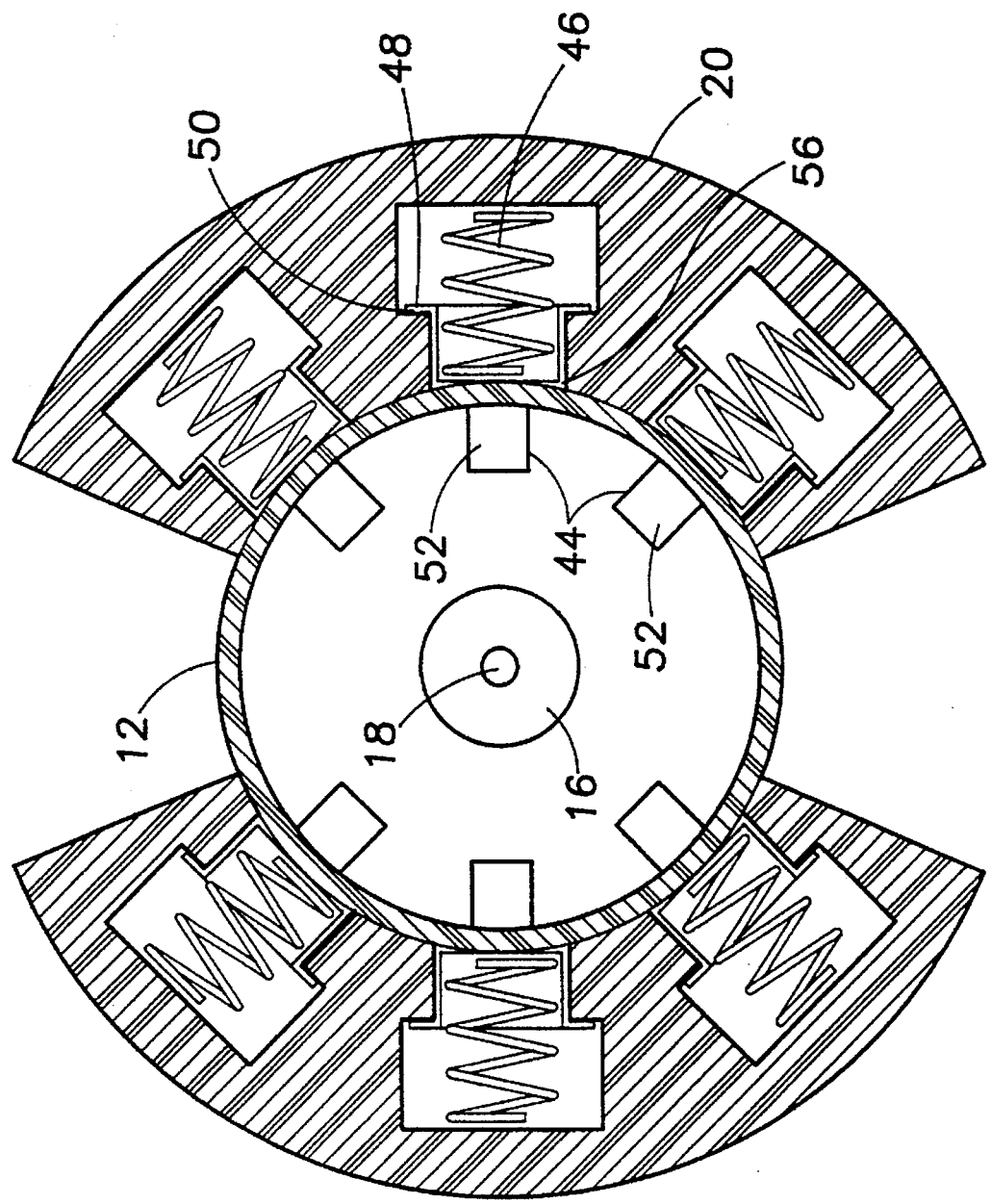
FIG. 4 is a cross sectional view of the invention taken along lines 4—4 of FIG. 3.

FIG. 4 shows that part of the locking system within the enclosures 20. In this case six detents are utilized, however more or less could be used within the scope of this invention. The detent operates as explained and each chamber is protected from the fluid entering it by a small seal 56 located between the detent and the wall of the barrel.

Figure 5:
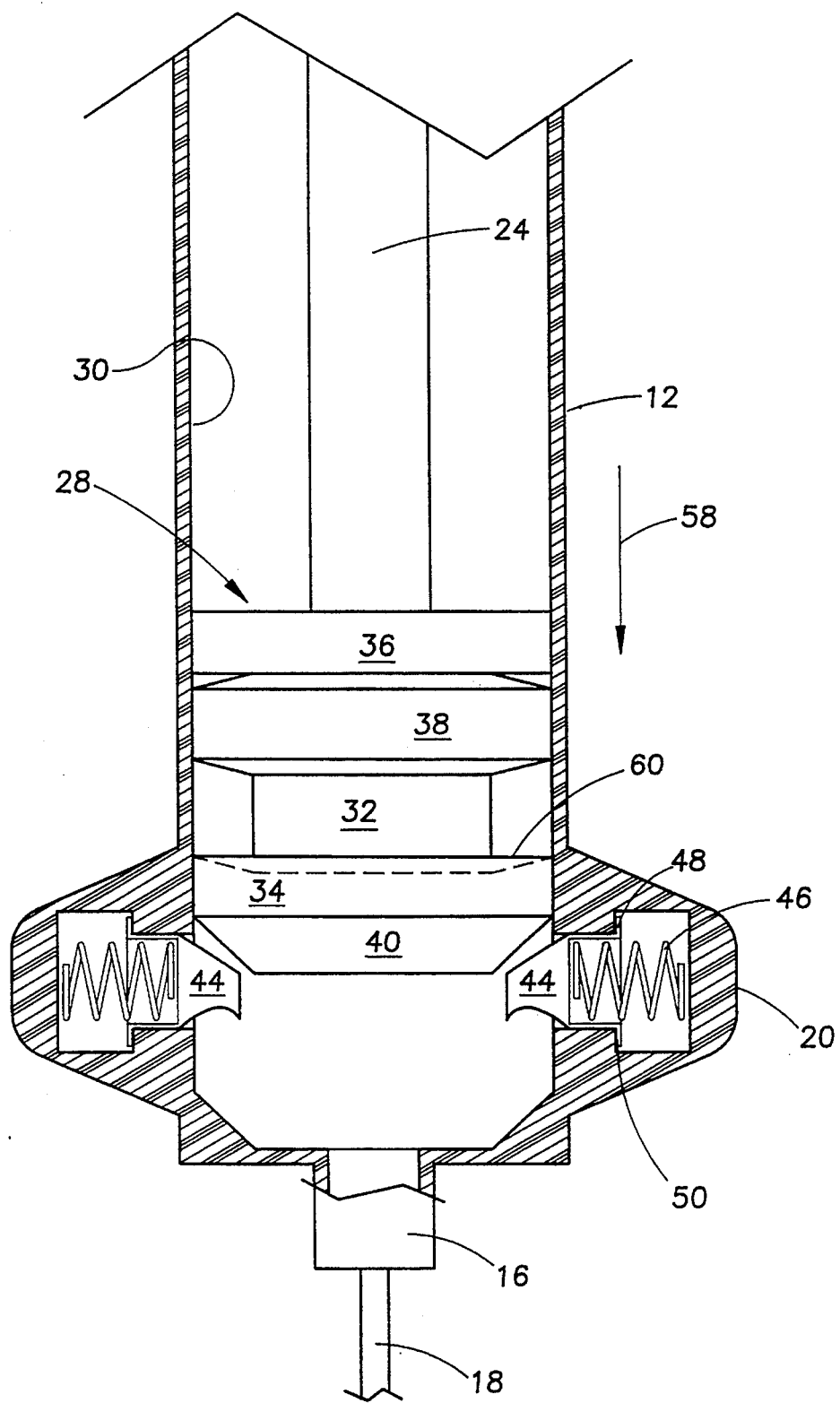
FIG. 5 is a cutaway view of the invention showing the arrangement of components in the dispensing condition.

Referring to FIG. 5, with the piston 28 moving in the direction of arrow 58 the floating ring 38 has moved against the trailing edge 36 of the piston. Leading edge 60 of the piston head 34 is exposed and able to be engaged by the locking detents 44. This condition is created by causing the floating ring to have a substantially tighter fit with the interior wall 30 of the barrel than with channel 32.

Figure 6:
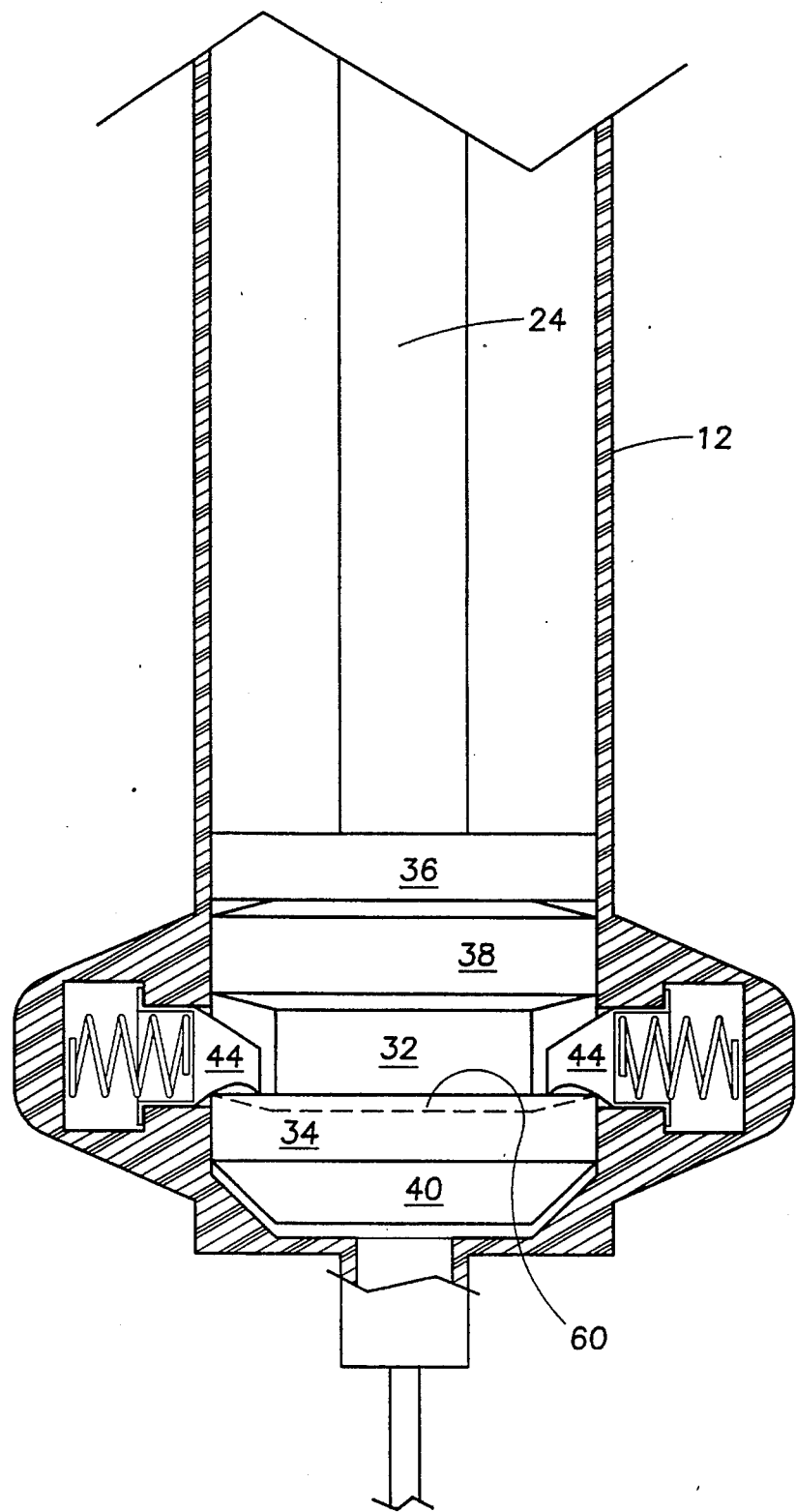
FIG. 6 is a cutaway view of the invention showing the arrangement of components in the closed or locked condition.

In FIG. 6 the locking detents 44 are seen engaging the surface 60 of the piston head 34 in the locked condition. The shaft 24 is so constructed that in the event a force is applied to withdraw the piston, the shaft will disengage and simply pull out of the barrel.

It should be understood, of course, that the foregoing disclosure relates to only a preferred embodiment of the invention and that numerous modification of alteration may be made therein without departing from the spirit and scope of the invention as set forth in the appended claims.

What is claimed is:

1. A locking system for hypodermic syringes comprising: a cylindrically shaped barrel having a first and a second end, wherein said first end is open and said second end is closed, with a brace having an aperture for receiving a hypodermic needle communicating with the interior of the said barrel; a cylindrically shaped piston, having a channel circumferentially located between the ends thereof, mounted in fluid tight relation with the interior wall of the barrel and adapted for axial translation within the barrel; a piston shaft attached to the piston and extending along the longitudinal axis of the barrel and beyond the limits of the first end of said barrel; a floating ring positioned within the channel of the piston engaging the interior wall of the barrel, and a plurality of spring biased detent means positioned peripherally around the barrel and adapted to extend into the barrel for engaging the channel of said piston, whereby dislocation of the floating ring by movement of the piston will allow the detent means to move into the cylinder and restrain the piston from further movement after the piston moves past the said detents.

2. A locking system for hypodermic syringes according to claim 1 wherein: the floating ring restrains the locking detents from engaging the channel of the piston.

* * * * *